United States Patent
Phukan et al.

(10) Patent No.: US 9,804,296 B2
(45) Date of Patent: Oct. 31, 2017

(54) HYDROPHILIC MACROMERS AND HYDROGELS COMPRISING THE SAME

(71) Applicants: Monjit Phukan, Bangalore (IN);
Anubhav Saxena, Bangalore (IN);
Shreedhar Bhat, Bangalore (IN)

(72) Inventors: Monjit Phukan, Bangalore (IN);
Anubhav Saxena, Bangalore (IN);
Shreedhar Bhat, Bangalore (IN)

(73) Assignee: MOMENTIVE PERFORMANCE MATERIALS INC., Waterford, NY (US)

( * ) Notice: Subject to any disclaimer, the term of this patent is extended or adjusted under 35 U.S.C. 154(b) by 0 days.

(21) Appl. No.: 14/492,433

(22) Filed: Sep. 22, 2014

(65) Prior Publication Data

US 2015/0011669 A1     Jan. 8, 2015

Related U.S. Application Data

(63) Continuation of application No. PCT/US2013/029358, filed on Mar. 6, 2013.

(60) Provisional application No. 61/614,240, filed on Mar. 22, 2012.

(51) Int. Cl.
*G02B 1/04* (2006.01)
*C08F 290/06* (2006.01)
*C09D 151/08* (2006.01)
*C09J 151/08* (2006.01)
*C07F 7/08* (2006.01)

(52) U.S. Cl.
CPC ............ *G02B 1/043* (2013.01); *C07F 7/0818* (2013.01); *C08F 290/062* (2013.01); *C08F 290/068* (2013.01); *C09D 151/08* (2013.01); *C09J 151/08* (2013.01); *G02B 2207/109* (2013.01)

(58) Field of Classification Search
USPC ...................................... 523/107; 528/25, 32
See application file for complete search history.

(56) References Cited

U.S. PATENT DOCUMENTS

| | | | |
|---|---|---|---|
| 3,507,923 A | 4/1970 | Donald et al. | |
| 4,150,048 A | 4/1979 | Schilling et al. | |
| 4,260,725 A * | 4/1981 | Keogh ................. | C08F 230/08 264/1.1 |
| 4,486,577 A * | 12/1984 | Mueller ............. | C08F 290/148 351/159.33 |
| 4,962,218 A | 10/1990 | Blevins et al. | |
| 5,070,166 A | 12/1991 | Su et al. | |
| 5,352,714 A | 10/1994 | Lai et al. | |
| 5,981,669 A | 11/1999 | Valint et al. | |
| 5,998,498 A | 12/1999 | Vanderlaan et al. | |
| 6,013,711 A * | 1/2000 | Lewis ................... | A61K 6/083 524/265 |
| 6,207,782 B1 | 3/2001 | Czech et al. | |
| 6,867,245 B2 * | 3/2005 | Iwata .............. | B29D 11/00125 264/1.32 |
| 7,268,189 B2 | 9/2007 | Muller et al. | |
| 7,572,841 B2 * | 8/2009 | Chen ..................... | G02B 1/043 351/159.33 |
| 8,686,099 B2 * | 4/2014 | Guyer ................... | C07F 7/0852 523/105 |
| 2003/0162862 A1 | 8/2003 | McCabe et al. | |
| 2008/0231798 A1 | 9/2008 | Zhou et al. | |
| 2009/0143499 A1 | 6/2009 | Chang et al. | |
| 2010/0296049 A1 | 11/2010 | Justynska et al. | |
| 2010/0298446 A1 | 11/2010 | Chang et al. | |
| 2011/0166248 A1 | 7/2011 | Hsu et al. | |

FOREIGN PATENT DOCUMENTS

| | | |
|---|---|---|
| EP | 885932 A2 | 12/1998 |
| WO | 2010038242 A2 | 4/2010 |

OTHER PUBLICATIONS

ISA/US, International Search Report and Written Opinion, prepared for PCT/US2013/029358, dated May 21, 2013.

* cited by examiner

*Primary Examiner* — Tae H Yoon
(74) *Attorney, Agent, or Firm* — Joseph Ostroff; McDonald Hopkins LLC

(57) ABSTRACT

A hydrophilic silicone macromer composition suitable for use in producing hydrogel polymer films from which biomedical devices such as contact lenses can be made. The hydrophilic silicone macromer comprises a polyether backbone comprising a silicone-containing pendant group. In one aspect, a hydrophilic silicone macromer is of the Formula 1:

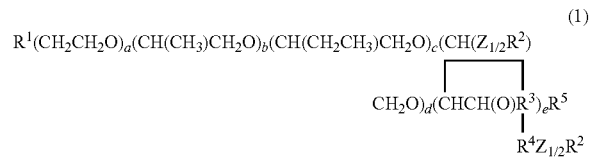

The hydrophilic silicone macromer can be used to form a polymer and a hydrogel film suitable for forming contact lenses.

21 Claims, No Drawings

HYDROPHILIC MACROMERS AND HYDROGELS COMPRISING THE SAME

CROSS REFERENCE TO RELATED APPLICATIONS

This application is a continuation of International Patent Application No.: PCT/US2013/029358, entitled "Hydrophilic Macromers And Hydrogels Comprising The Same", filed on Mar. 6, 2013, which claims the priority benefit of U.S. Provisional Patent Application No. 61/614,240, entitled "Hydrophilic Macromers And Hydrogels Comprising The Same", filed on Mar. 22, 2012, each of which are hereby incorporated in their entirety by reference.

FIELD OF THE INVENTION

The present invention relates to compositions comprising a hydrophilic organo-modified silicone-containing macromer. The present invention provides, in one aspect, polyether macromers capable of undergoing free-radical polymerization and having a silicone-containing pendant group. The present invention also relates to hydrogel compositions and films suitable for producing biomedical products including contact lenses.

BACKGROUND

Silicone-hydrogel films are used to make extended wear soft contact lenses due to their relatively high oxygen permeability, flexibility, comfort, and reduced corneal complications. Conventional hydrogel materials (e.g. 2-hydroxyethylmethacrylate, HEMA) by themselves have poor oxygen permeability and they transport oxygen to the eye through the absorbed water molecules. Water has low oxygen permeability, also called the Dk value, which may be expressed in Barrer, wherein 1 Barrer=$10^{-11}$ (cm$^3$ O$_2$) cm cm$^{-2}$ s$^{-1}$ mmHg$^{-1}$ where "cm$^3$ O$_2$" is at a quantity of oxygen at standard temperature and pressure and where "cm" represents thickness of the material and "cm$^{-2}$" is the reciprocal of the surface area of that material. The Dk of water is 80 Barrer. Upon exposure to atmospheric air for long periods, these lenses are slowly dehydrated and the amount of oxygen transported to the cornea is reduced. Eye irritation, redness and other corneal complications can result and hence restrict use of the lenses to limited periods of wear.

Silicone-hydrogels with the comfort of soft contact lenses and significantly higher oxygen permeability overcame the obstacles for periods of wear beyond conventional hydrogels and were revolutionary in the field of optometry. The following patents describe silicone-hydrogels for use in contact lenses.

U.S. Pat. No. 4,260,725, assigned to Bausch & Lomb Inc., describes a water absorbing, soft, hydrophilic, flexible, hydrolytically stable, biologically inert contact lens with the capability of transporting oxygen sufficiently to meet the requirements of the human cornea comprising a polysiloxane which is am terminally bonded through divalent hydrocarbon groups to polymerizably activated unsaturated groups and which contain hydrophilic side-chains.

U.S. Pat. No. 5,352,714, assigned to Bausch & Lomb Inc., describes silicone-containing hydrogels with enhanced wettability comprising a silicone-containing monomer, hydrophilic monomers, and a relatively non-polar ring-containing monomer able to be converted to a highly polar amino acid upon hydration.

U.S. Pat. No. 5,998,498, assigned to Johnson & Johnson Vision Products describes a silicone hydrogel prepared by curing a reaction mixture comprising a silicone-containing monomer having the following structure:

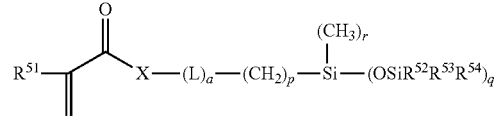

wherein $R^{51}$ is H or CH$_3$, q is for 2 and for each q, $R^{52}$, $R^{53}$ and $R^{54}$ are independently ethyl, methyl, benzyl, phenyl or a monovalent siloxane chain comprising from 1 to 100 repeating Si—O units, p is 1 to 10, r=(3−q), X is 0 or NR$^{55}$, where $R^{55}$ is H or a monovalent alkyl group with 1 to 4 carbons, a is 0 or 1, and L is a divalent linking group which preferably comprises from 2 to 5 carbons, which may also optionally comprise ether or hydroxyl groups, for example, a polyethylene glycol chain.

U.S. Pat. No. 6,867,245, assigned to Asahikasei Aime Co., describes a soft contact lens, and provides a contact lens that shows small and stable contact angle to water at its surface in water as well as in air, little deposition in wearing, high oxygen permeability, no adhesion of lens to a cornea, and superior extended-wearing characteristics. It describes a hydrogel soft contact lens, which has a contact angle at a lens surface in a range of 10-50° by the captive bubble method in water and 3 & 90° by the sessile drop method in air, oxygen permeability of not less than 30 Dk and water content of not less than 5%, and also a hydrogel soft contact lens consisting of a polymer comprising a hydrophilic siloxanyl monomer shown by a specified general formula. This patent discloses copolymers of hydrophilic siloxane with amide-group containing monomers that are stated as being useful materials for contact lenses. The polymer comprises hydrophilic amide-group containing siloxanyl methacrylate, a siloxanyl methacrylate (3-tris[trimethylsiloxy]silylpropylmethacrylate, abbreviated as TRIS) including a hydrophilic polyether modified siloxanyl alkyl methacrylate and a cross-linkable monomer.

U.S. Pat. No. 6,013,711, assigned to the CK Witco Corporation describes a method for improving the miscibility of the lower molecular weight unsaturated siloxane-polyether copolymers with the α,ω-divinylpolysiloxanes without loss of storage stability, or delay of cure at the vulcanization temperature, or loss of permanent hydrophilicity or other desirable features of the cured polysiloxane. The compositions comprise one or more α,ω-divinylpolysiloxanes, unsaturated polysiloxane-polyether copolymers having from 2 to 5 silicon atoms per molecule, which are preferably trisiloxanes, and a compatibilizing additive. The permanently hydrophilic, rapidly wettable polysiloxane compositions yield static water contact angles <50° and dynamic advancing contact angles of less than about 100.

U.S. Pat. No. 6,207,782 assigned to Crompton Corporation discloses acrylated hydrophilic polysiloxanes monomers and polymers and their copolymers with acrylate/methacrylate co-monomers and their emulsions for personal care, textile and coating applications. The acrylated siloxanes are represented by formula (a):

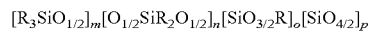

wherein R is selected from the $R^1$ and P, each $R^1$ can be the same or different and each is a monovalent hydrocarbon group; each P is $R^3[O(C_bH_{2b}O)_zCOCR^4=CH_2]_g$, $R^3$ is a polyvalent organic moiety, which may be hydroxy substituted alkylene, g is the valency of $R^3$ minus 1, $R^4$ is hydrogen or methyl; b=2 to 4, preferably 2 to 3; z=1 to 1000, preferably 3 to 30; and m+n+p+o=1 to 100, preferably 2 to 20, at least one R is P; n=1 to 100; when o is not zero n/o<10:1; when p is not zero n/p<10:1; and m=0 to 10. A preferred acrylated siloxane of the '782 is of the Formula (b):

wherein x, and y can be 0 or an integer, preferably each x and y are from 0 to 100, most preferably 0 to 25; Q can be $R^1$ or P, with the proviso that the average acrylate functionality is >1 unsaturated groups per molecule with the preferred embodiment having y=0 and Q=P.

Conventionally, silicone-hydrogels are made by polymerizing the acrylate or methacrylate functionalized silicone monomer with organic (hydrophilic) monomers, such as 2-hydroxyethyl methacrylate (HEMA), N-vinylpyrrolidone (NVP), methyl methacrylic acid (MMA), and N,N-dimethylacrylamide (DMA), etc., in the presence of cross-linker and free radical initiators (actinic). Cross-linking agents generally have two or more reactive functional groups at different sites of the molecule. Typically, these sites contain polymerizable ethylenic unsaturation groups. During curing, they form a covalent bond with two different polymer chains and form a stable three-dimensional network to improve the strength of the polymer. Cross-linking agents conventionally used in contact lenses include ethylene glycol dimethacrylate and trimethyloylpropane trimethacrylate (about 0.1 to 2 wt. %). Other useful cross-linking agents include diethyleneglycol dimethacrylate, bisphenol A dimethacrylate, diglycidyl bisphenol A dimethacrylate, dimethacrylate-terminated polyethylene glycol, and reactive linear polyether modified silicones.

Generally, silicone hydrogel contact lens materials are made using either hydrophobic mono-functional silicone monomer (such as TRIS) or multi-functional hydrophilic silicone monomer followed by secondary surface treatment. Mono-functional silicone monomers are preferred in the contact lens industry over multi-functional silicone monomers since the latter lead to increased rigidity of the lens made therefrom.

The state of this art for soft contact lenses, including the silicone-based materials described in the above mentioned patents, still possess major shortfalls like sub-optimal surface wettability and lipid deposition. In an effort to overcome these drawbacks, current state of the art technology uses either expensive secondary surface treatments called "plasma oxidation" or use internal wetting agents at the expense of oxygen permeability. Hence there remains a need for hydrophilic silicone monomers with inherently advantageous wettability and oxygen permeability that can be used to make contact lenses without the drawbacks and expensive surface treatments necessary with the silicone containing materials of the present art.

SUMMARY

The present invention discloses a composition comprising a new functionalized silicone macromer containing a polyether moiety with a silicone-containing pendant group, processes to produce such macromers with high purity and ease of manufacturability and homo and copolymers made from these monomers that have greater hydrophilic functionality. The compositions comprising the functionalized silicone macromers of the present invention are useful to make water-absorbing, oxygen-permeable silicone-hydrogel films that can be fashioned into extended wear soft contact lens.

In one aspect, the present invention provides a composition comprising a hydrophilic silicone macromer described by the general structure of Formula 1:

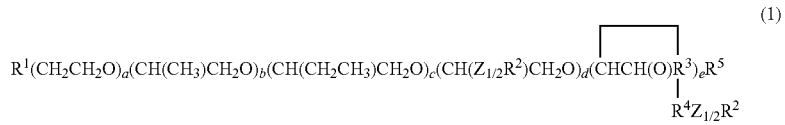

wherein $R^2$ is a group defined as $M_f D_g T_h Q_i R^6_j$ with $M=R^7 R^8 R^9 SiZ_{1/2}$, $D=R^{10} R^{11} SiZ_{2/2}$, $T=R^{12} SiZ_{3/2}$, $Q=SiZ_{4/2}$, $R^6=$—$(CH_2)_{1/2}(R^{13})_k(CH_2)_{1/2}$—; $R^1$ is independently selected from —OH, —OC(O)$R^{15}$, Y, or —OR$^{15}$; $R^5$ is independently selected from hydrogen, a —C(O)$R^{15}$ group, Y, or a monovalent hydrocarbon radical having from about 1 to about 40 carbon atoms that optionally contain a heteroatom and/or a hydroxyl group; at least one of $R^1$ and $R^5$ is Y; Y is a free radical polymerizable group; Z is O or a $CH_2$ group subject to the limitation that the molecule contains an even number of $O_{1/2}$ and an even number of $(CH_2)_{1/2}$ groups and they both are all paired in the molecule; $R^3$ is a trivalent hydrocarbon radical having 1 to about 40 carbon atoms optionally containing a heteroatom and/or a hydroxyl group; $R^7$, $R^8$, $R^9$, $R^{10}$, $R^{11}$, $R^{12}$, and $R^{15}$ are each independently selected from OR$^{14}$, a monovalent hydrocarbon radical having 1 to about 20 carbon atoms that optionally contain a heteroatom and/or a hydroxyl group; $R^4$ is a divalent, linear, or branched unsaturated or saturated hydrocarbon radical containing at least one to about 30 carbon atoms that optionally contain a heteroatom and/or a hydroxyl group; $R^{13}$ is oxygen or divalent linear or branched unsaturated or saturated hydrocarbon radicals containing at least one to about 30 carbon atoms that optionally contain a heteroatom and/or a hydroxyl group; $R^{14}$ is a monovalent, linear or branched unsaturated or saturated hydrocarbon radical having 1 to about 20 carbon atoms that optionally contain a heteroatom and/or a hydroxyl group; a+e>2; b, c, and d are zero or positive subject to the limitation 3<a+b+c+d+e<about 1000; d+e>1; f, g, h, i and j are 0 or positive subject to the limitation f+g+h+i+j<about 300; and k is either 0 or 1.

In another aspect, the present invention provides polymers, e.g., homopolymers or copolymers, comprising the hydrophilic silicone macromers.

In still another aspect, the present invention provides a hydrogel composition comprising the hydrophilic silicone macromers such as, for example, a hydrophilic silicone macromer of Formula (1). In one embodiment, the hydrogel composition comprises (a) a hydrophilic silicone macromer in accordance with aspects of the invention, (b) a free-radical polymerizable organic monomer, (c) an initiator, and (d) optionally a cross-linker.

Silicone hydrogel films produced with these monomers offer improved curing kinetics, surface wettability, oxygen permeability, mechanical properties and post cure extractions in comparison to silicone-hydrogel films prepared from monomers having linear alkyl linking groups, such as those already disclosed in the prior art for contact lens applications.

DETAILED DESCRIPTION

In accordance with aspects of the present invention, new hydrophilic silicone monomers having a branched silicone containing group and are useful for preparing water-absorbing silicone hydrogel films that can be used in contact lens applications are described. Silicone hydrogel films obtained with these monomers show excellent wettability, oxygen permeability, and desirable modulus in comparison to previously known films.

As used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

A "macromer" refers to a medium and high molecular weight compound that can comprise one or more functional groups capable of being polymerized, cross-linked, or both.

A "monomer" refers to a relatively low molecular weight compound that is polymerizable.

A "hydrophilic" substance (e.g., hydrophilic monomer, hydrophilic macromer, hydrophilic polymer, etc.) is one that is water-loving, has an affinity for water, is capable of absorbing water, etc. A hydrophilic substance may be soluble or insoluble (e.g., substantially insoluble) in water. A hydrophilic substance can, in one embodiment, contain both hydrophilic and hydrophobic portions, but the hydrophobic portions are present in relative amounts such that the substance or component is hydrophilic. In one embodiment, a hydrophilic substance can absorb at least 10 percent by weight water.

"Homopolymers" are polymers made from the same repeating macromer or monomer. "Copolymers" are polymers wherein the polymer contains at least two structurally different macromers, at least two structurally monomers, or at least one macromer and at least one monomer. Notations such as (meth)acrylate denote monomer with either acrylate or methacrylate functionality.

Hydrophilic Silicone Monomers

In one aspect, the present invention provides compositions comprising at least one hydrophilic silicone molecule comprising a polyether chain and a silicone-containing group pendant to the chain. The hydrophilic silicone molecules can be monomer or macromer described by the general structure of Formula 1:

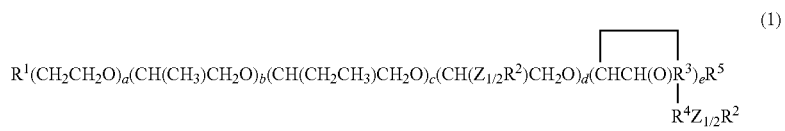

(1)

$$R^1(CH_2CH_2O)_a(CH(CH_3)CH_2O)_b(CH(CH_2CH_3)CH_2O)_c(CH(Z_{1/2}R^2)CH_2O)_d(CHCH(O)R^3)_eR^5$$
$$R^4Z_{1/2}R^2$$

wherein $R^2$ is a group defined as $M_fD_gT_hQ_iR^6_j$ with $M=R^7R^8R^9SiZ_{1/2}$, $D=R^{10}R^{11}SiZ_{2/2}$, $T=R^{12}SiZ_{3/2}$, $Q=SiZ_{4/2}$, $R^6=-(CH_2)_{1/2}(R^{13})_k(CH_2)_{1/2}-$; $R^1$ is independently selected from $-OH$, $-OC(O)R^{15}$, Y, or $-OR^{15}$; $R^5$ is independently selected from hydrogen, a $-C(O)R^{15}$ group, Y, or a monovalent hydrocarbon radical having from about 1 to about 40 carbon atoms that optionally contain a heteroatom and/or a hydroxyl group; at least one of $R^1$ and $R^5$ is Y; Y is a free radical polymerizable group; Z is O or $CH_2$ group subject to the limitation that the molecule contains an even number of $O_{1/2}$ and an even number of $(CH_2)_{1/2}$ groups and they both are all paired in the molecule; $R^3$ is a trivalent hydrocarbon radical having 1 to about 40 carbon atoms that optionally contain a heteroatom and/or a hydroxyl group; $R^7$, $R^8$, $R^9$, $R^{10}$, $R^{11}R^{12}$ and $R^{15}$ are each independently selected from $OR^{14}$, a monovalent hydrocarbon radical having 1 to about 20 carbon atoms that optionally containing a heteroatom and/or a hydroxyl group; $R^4$ is a divalent, linear, or branched unsaturated or saturated hydrocarbon radical containing at least one and less than about 30 carbon atoms that optionally contain a heteroatom and/or a hydroxyl group; $R^{13}$ is oxygen or a divalent linear or branched unsaturated or saturated hydrocarbon radical containing at least one and less than about 30 carbon atoms that optionally contain a heteroatom and/or a hydroxyl group; $R^{14}$ is a monovalent, linear or branched unsaturated or saturated hydrocarbon radical having 1 to about 20 carbon atoms that optionally contain a heteroatom and/or a hydroxyl group; a+e>2; b, c, and d are zero or positive subject to the limitation 3<a+b+c+d+e<about 1000; d+e>1; f, g, h, i and j are 0 or positive subject to the limitation f+g+h+i+j<about 300; and k is either 0 or 1.

The free radical polymerizable group Y can comprise any suitable polymerizable group. Examples of suitable molecules are acrylate, methacrylate, acrylamide, methacrylamide, vinyl, allyl, methallyl, and internal olefinic bond containing molecules such as, but not limited to, butenedioic acid, butenedioic esters or amides, itaconic acid, itaconic acid, esters, amides etc. In one aspect of the present invention, the organic molecules comprise substantially hydrophilic molecules with one free radical polymerization-effective group, for example, acrylic acid, methacylic acid, NVP, NIPAM, etc. In yet another aspect of the current invention, organic molecules can be selected from substantially less hydrophilic monomers with the limitation that the overall formulation is hydrophilic. In one embodiment, the polymerizable group Y comprises a group having the general structure of Formula 2:

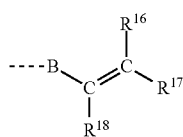
(2)

wherein $R^{16}$, $R^{17}$, and $R^{18}$ can be independently selected from hydrogen; substituted or unsubstituted monovalent alkyl groups with 1 to 10 carbon atoms that optionally contain a heteroatom, —COOH; and —CH$_2$COOH; B can be independently selected from a divalent radical containing 1 to 20 carbon atoms that can optionally contain a heteroatom or from the following functional moieties:

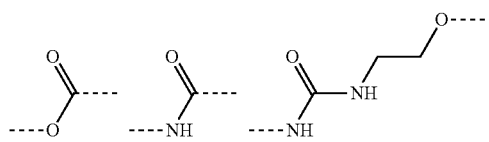

-continued

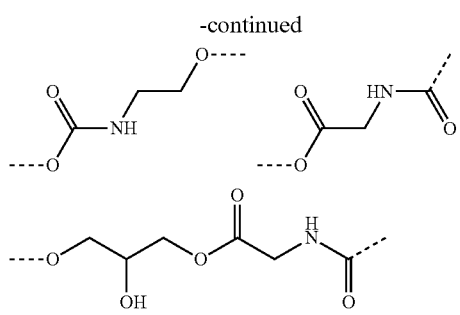

In one embodiment, B can be selected from a —C(O) group, —NR$^{19}$C(O)— where R$^{19}$ is H or a monovalent alkyl or aralkyl radical containing 1 to 50 carbon atoms that optionally contain a heteroatom. In yet another embodiment B can be selected from —(CR$^{20}$R$^{21}$)$_p$OC(O)(CR$^{22}$R$^{23}$)$_q$NR$^{19}$C(O)— or —C(O)(CR$^{22}$R$^{23}$)$_q$NR$^{19}$C(O)— wherein R$^{20}$, R$^{21}$, R$^{22}$ and R$^{23}$ can independently selected from H, OH, a monovalent hydrocarbon with 1 to 20 carbon atoms that optionally contain a heteroatom, and subscripts p and q can take values from 1 to 10.

In one embodiment, the polymerizable hydrophilic organo-modified silicone molecule generally described by Formula 1 can be a compound having the following structure according to Formula 3:

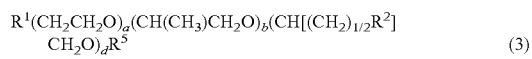
(3)

where $R^2$ is a group defined as $M_fD_gT_hQ_iR^6_j$ with M=R$^7$R$^8$R$^9$Si(O)$_{1/2}$; D=R$^{10}$Si(O)$_{2/2}$(CH$_2$)$_{1/2}$; f=2; g=1; h=0; i=0; j=1; and R$^6$=—(CH$_2$)$_{1/2}$R$^{13}$(CH$_2$)$_{1/2}$—; R1 and R5 are as described above; and a, b, and d are positive integers.

In another embodiment, the free radical polymerizable hydrophilic organo-modified silicone molecule generally represented by Formula 1 can be selected to provide a monomer having structure according to Formula 4:

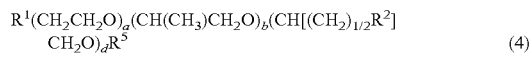
(4)

where $R^2$ is a group defined as $M_fD_gT_hQ_iR^6_j$ with M=R$^7$R$^8$R$^9$Si(O)$_{1/2}$; T=Si(O)$_{3/2}$(CH$_2$)$_{1/2}$; f=3; g=0; h=1; i=0; j=1; and R$^6$=—(CH$_2$)$_{1/2}$R$^{13}$(CH$_2$)$_{1/2}$—.

In another embodiment, the hydrophilic organo-modified silicone molecule can have a structure according to Formula 5:

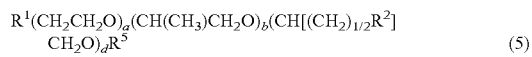
(5)

where $R^2$ is a group defined as R$^7$R$^8$R$^9$SiO(Si(R$^{10}$)(R$^{11}$)O)$_l$Si(R$^7$)(R$^8$)(CH$_2$)$_{1/2}$; and where 0≤l≤50.

In still another embodiment, the hydrophilic silicone molecule comprises a compound having the following Formula 6:

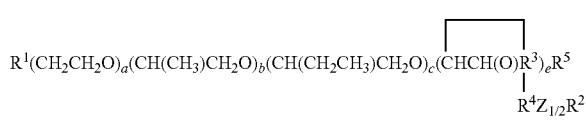
(6)

where $R^2$ is a group defined as R$^7$R$^8$R$^9$SiO(Si(R$^{10}$)(R$^{11}$)O)$_l$Si(R$^7$)(R$^8$)(CH$_2$)$_{1/2}$; and where 0≤l≤200.

In an exemplary embodiment, the free radical polymerizable hydrophilic silicone molecule comprises a random or block copolymer having a structure of Formula 7:

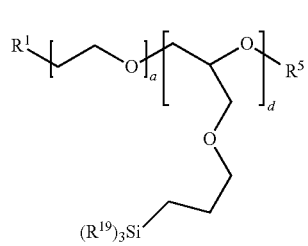
(7)

wherein $R^1$ is independently selected from —OH, —OC(O)R$^{15}$, —OR$^{15}$, or Y; R$^5$ is independently selected from hydrogen, a —C(O)R$^{15}$ group, a monovalent hydrocarbon radical having from about 1 to about 40 carbon atoms that optionally contains a heteroatom and hydroxyl group, or Y; Y is a free radical polymerizable group subject to the limitation that at least one of R$^1$ and R$^5$ is Y; R$^{19}$ is independently selected from linear, branched, or cyclic mono-valent radicals with 1 to 100 carbon atoms that may contain a heteroatom such as halogens, oxygen, nitrogen, or siloxane radicals containing 1 to 50 Si—O linear or cyclic linkages; a and d are non-zero integers such that $2 \leq a+d \geq 1000$, in one embodiment $2 \leq a+d \geq 100$, and in another embodiment $5 \leq a+d \geq 50$.

In yet another exemplary embodiment, the free radical polymerizable hydrophilic silicone macromer comprises a random or block copolymer having a structure of Formula 8:

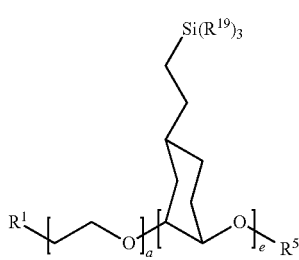

(8)

wherein $R^1$ is independently selected from —OH, —OC(O)$R^{15}$, —OR$^{15}$, or Y; $R^5$ is independently selected from hydrogen or a —C(O)R$^{15}$ group or a monovalent hydrocarbon radical having from about 1 to about 40 carbon atoms that optionally contains a heteroatom and a hydroxyl group, or Y; Y is a free radical polymerizable group subject to the limitation that at least one of $R^1$ and $R^5$ is Y; $R^{19}$ is independently selected from linear, branched, or cyclic mono-valent radicals with 1 to 100 carbon atoms that optionally contain heteroatoms such as halogens, oxygen, nitrogen, or siloxane radicals containing 1 to 50 Si—O linear or cyclic linkages; a and d are non-zero integers such that $2 \leq a+e \geq 1000$, more preferably $2 \leq a+e \geq 100$ and even more preferably $5 \leq a+e \geq 50$.

Polymers and Hydrogels

The hydrophilic silicone macromers may be used to form polymer compositions. The polymers may be homopolymers or copolymers. In one embodiment, the hydrophilic silicone macromers may be used to form homopolymers comprising one of the inventive monomers. In another embodiment, the hydrophilic silicone monomers may be used to form copolymers comprising (1) two or more structurally different hydrophilic silicone macromers, and/or (2) one or more hydrophilic silicone macromers and another monomer such as, for example, monomers suitable for use in forming silicone hydrogels.

In one embodiment, the copolymer comprises an inventive hydrophilic silicone macromer and a hydrophilic unsaturated organic monomer suitable for use in silicone hydrogels. In one embodiment for making silicone hydrogels, the organic monomer is chosen from a vinylic monomer, an acrylide monomer, an acrylic monomer, or a combination of two or more thereof. Non-limiting examples of suitable vinylic monomers include, N-vinyl-pyrrolidone, N-vinyl-caprolactam, N-vinyl-acetamide, N-vinyl-formamide and N-vinyl-isopropylamide, vinyl benzene, vinyl naphthalene, vinyl pyridine, vinyl alcohol, vinyl containing silicones, or a combination of two or more thereof. Non-limiting examples of suitable acrylic include 2-hydroxy-ethyl-methacrylate (HEMA), 2-hydroxy-ethyl-acrylate (HEA), hydroxyl propyl methacrylate, trimethylammonium 2-hydroxy propyl methacrylate hydrochloride, dimethylaminoethyl methacrylate, glycerol methacrylate, N,N-dimethylacrylamide, N-isopropylacrylamide, acrylamide, methacrylamide, acrylic acid, methacrylic acid, acrylated hydrophilic or hydrophobic organo-silicones, or combinations of two or more thereof. In an exemplary embodiment, the organic monomer is chosen from N,N-dimethylacrylamide, 2-hydroxy-ethyl-methacrylate (HEMA), N-vinylpyrrolidone, methacrylic acid, or a combination of two or more thereof.

The ratio of the silicone monomer of the present invention to the other hydrophilic unsaturated organic monomers is from 1:100 to about 100:1. Monomers and polymers with linear alkyl linked (meth)acrylated silicone polyether chains means those compounds without any branching in the linking group that connects the siloxane with the polyalkylene oxide part of the side chain in such compounds. Notations such as (meth)acrylate denote monomer with either acrylate or methacrylate functionality. The macromers of the present invention can be used to obtain cured elastomers with desirable physical strength and resistance to tearing after absorption of water. The mono-(meth)acrylate functionalized silicone monomers/polymers of the present invention and their preparation and use in contact lens are further described in the sections below.

In one embodiment, the present invention provides a hydrogel composition comprising (a) a hydrophilic silicone macromer in accordance with aspects of the invention, (b) a free-radical polymerizable organic monomer, (c) an initiator, and (d) optionally a cross-linking agent. The hydrophilic silicone macromer and free-radical polymerizable organic monomer can be as described above. The cross-linking agent can generally have two or more reactive functional groups at different sites of the molecule. Typically, these sites contain polymerizable ethylenic unsaturation groups. During curing, they form a covalent bond with two different polymer chains and form a stable three-dimensional network to improve the strength of the polymer. Cross-linking agents conventionally used in contact lenses include ethylene glycol dimethacrylate and trimethyloylpropane trimethacrylate (about 0.1 to 2 wt. %). Other useful cross-linking agents include, but are not limited to, diethyleneglycol dimethacrylate, bisphenol A dimethacrylate, diglycidyl bisphenol A dimethacrylate, dimethacrylate-terminated polyethylene glycol, and reactive linear polyether modified silicones.

Initiators, for example, can be selected from materials well known for such use in the polymerization art, and may be included in the lens-forming material in order to promote, and/or increase the rate of, the polymerization reaction. An initiator is a chemical agent capable of initiating polymerization reactions. The initiator can be a photoinitiator or a thermal initiator.

A photoinitiator can initiate free radical polymerization and/or cross-linking by the use of light. Suitable photoinitiators are benzoin methyl ether, diethoxyacetophenone, a benzoylphosphine oxide, 2-hydroxy-2-methyl propiophenone (HMPP), 1-hydroxycyclohexyl phenyl ketone and Darocur and Irgacure types, preferably Darocur® 1173 and 2959. Examples of benzoylphosphine initiators include 2,4, 6-trimethylbenzoyldiphenylophosphine oxide; bis-(2,6-dichlorobenzoyl)-4-N-propylphenylphosphine oxide; and bis-(2,6-dichlorobenzoyl)-4-N-butylphenylphosphine oxide. Reactive photoinitiators which can be incorporated, for example, into a macromer or can be used as a special monomer are also suitable. Examples of reactive photoinitiators are those disclosed in EP 632329, herein incorporated by reference in its entirety. The polymerization can then be triggered by actinic radiation, for example light, in particular UV light of a suitable wavelength. The spectral requirements can be controlled accordingly, if appropriate, by addition of suitable photosensitizers Examples of suitable thermal initiators include, but are not limited to, 2,2'-azobis(2,4-dimethylpentanenitrile), 2,2'-azobis(2-methylpropanenitrile), 2,2'-azobis(2-methylbutanenitrile), peroxides such as benzoyl peroxide, and the like. Preferably, the thermal initiator is 2,2'-azobis(2-methylpropionitrile) (AIBN).

The polymers of this invention may also contain ultraviolet absorbents, pigments and colorants in the form of additives or co-monomers. The present invention also provides silicone-hydrogel compositions comprising (meth) acrylate functionalized hydrophilic silicone monomer and conventional monomer such as HEMA or other contact lens monomers to produce soft, flexible water absorbing films. The homo and copolymers of the present invention are clear (no haze from poor miscibility) polymers that absorb about 10 wt. % to about 60 wt. % of water, showing excellent surface wettability and effective oxygen permeability, all of which are necessary for the better comfort when lens are worn and for good health of the human cornea. The present invention also provides contact lenses made from the silicone-hydrogel films of the claimed invention. These embodiments are further described below.

To form polymers using the monomers of the present invention, the desired monomers are mixed and the resulting mixture is polymerized and cured to form transparent thin films by known thermal or UV cure techniques, using either peroxides or photoinitiators in the presence of cross-linking agents. The monomers added to the monomer mix to create the mixture prior to polymerization to form the polymers may be monomers or prepolymers. A "prepolymer" is a reaction intermediate polymer of medium molecular weight having polymerizable groups. Thus it is understood that the terms "silicone-containing monomers" and "hydrophilic monomers" include prepolymers. The present invention is also directed to silicone hydrogel films comprising the homopolymers or copolymers detailed above.

The macromers with high molecular weight polyether chains produced in the current invention may be used to form hydrophilic silicone homo/copolymers that produce silicone-hydrogel films having better oxygen permeability and significantly improved surface wettability in comparison to monomers with linear alkyl linking groups in the polyether chains. The contact lenses produced from the silicone-hydrogel films of the present invention do not require any expensive secondary treatments, like plasma oxidation or plasma coating, or internal wetting agents to improve wettability. That is, the contact lenses produced from silicone-hydrogel films of the present invention, without secondary treatment, are soft, flexible and inherently wettable and exhibit high oxygen permeability.

The polymers of the present invention form a clear, transparent homogeneous single-phase solution that can be cured directly without employing any additional homogenizing solvents, depending on the molecular weight of the present siloxane monomers, which are miscible with hydrophilic hydrogel monomers. Calculated solubility parameter values based on Fedors method (Robert F. Fedors, *Polymer Engineering and Science*, February 1974, vol. 14, No. 2) for the present inventive monomers range from approximately 16.5 to approximately 19 $(J/mol)^{1/2}$, which is closer to the solubility parameter value of conventional hydrogel monomers (such as HEMA, NVP and DMA) than silicone monomers such as TRIS. Miscibility is realized if the difference in solubility parameter between the instant inventive monomers and the hydrophilic co-monomers is less than about 7.7 $(J/mol)^{1/2}$.

In another embodiment of the present invention, the polymers may be formed into silicone-hydrogel films, via processes known in the art. The silicone-hydrogel films of the present invention are soft, flexible and highly transparent. Silicone-hydrogel films made from the inventive monomers exhibit better surface wettability and oxygen permeability compared to ones made using monomers having linear alkyl linked methacrylated silicone polyether chains. The present silicone hydrogel films are found to have dynamic advancing contact angles with water, in the range of 100° to 20° and absorb about 10 to 70 wt. % of water, which can vary depending on the molecular weight of the polyethers. The contact angle can also be altered in the defined range by adding wetting agents like poly(vinylpyrrolidone), poly(vinyl alcohol), and hydroxyalkyl cellulose. The silicone hydrogels produced were also found to have good mechanical properties (such as low modulus and high tear strength) required for the contact lens application.

Conventional silicone-hydrogel films are generally produced by curing a mixture of hydrophobic silicone monomers and hydrophilic hydrogel monomers in the presence of about 10 to 40 wt. % of solvent, as they are incompatible with each other. However in the current invention, the inventive hydrophilic silicone macromers are found to be miscible with conventional hydrophilic hydrogel monomers (such as HEMA, NVP and DMA) as well as conventional hydrophilic and hydrophobic siloxane mono/macro-mers and can form a homogeneous solution suitable to produce silicone-hydrogel films without employing any solvent.

The densities of the present macromers generally range from 0.89-1.1 g/cm$^3$ at 25° C. and the refractive index range from 1.4-1.46 for the sodium D line. The instant inventors have found that macromers with refractive index greater than 1.431 and density greater than 0.96 g/cm$^3$ produce completely miscible compositions or pseudo miscible compositions that appear homogeneous, clear and transparent with hydrophilic monomers like HEMA, in the absence of compatibilizing solvents. As has been stated above, conventional silicone monomers (for example, TRIS or 3-[Tris (trimethylsilyloxy)silyl]propyl methacrylate) must be mixed with hydrophilic monomers like HEMA in the presence of a solvent to get miscible compositions to make silicone hydrogels. The hydrogel co-monomer used to make silicone-hydrogel copolymers of the present invention can be hydrophilic acrylic monomers such as HEMA, N,N-Dimethylacrylamide (DMA), N-Vinylpyrrolidone (NVP), Methacrylic acid (MAA) etc.

The resulting polymers comprising the hydrophilic silicone macromers may be formed into silicone-hydrogel films, via processes known in the art. Accordingly, the present invention is also directed to contact lens produced from either homo or copolymers of the present invention. The monomers/polymers of the present invention can be formed into contact lenses by spin casting processes, as disclosed in U.S. Pat. Nos. 3,408,429 and 3,496,254, cast molding processes, as disclosed in U.S. Pat. Nos. 4,084,459 and 4,197,266, combinations of methods thereof, or any other known or late discovered method for making contact lenses. Polymerization may be conducted either in a spinning mold, or a stationary mold corresponding to a desired contact lens shape. The lens may be further subjected to mechanical finishing, as occasion demands. Polymerization may also be conducted in an appropriate mold or vessel to form buttons, plates or rods, which may then be processed (e.g., cut or polished via lathe or laser) to give a contact lens having a desired shape.

The relative softness or hardness of the contact lenses fabricated from the resulting polymer of this invention can be varied by decreasing or increasing the molecular weight of the polysiloxane prepolymer end-capped with the activated unsaturated group (such as methacryloxy) or by varying the percent of the co-monomer. Generally, as the ratio of polysiloxane units to end-cap units increases, the softness of the material increases.

The polymers of this invention may also contain ultraviolet absorbents, pigments and colorants in the form of additives or co-monomers.

As stated above, the silicone-hydrogels of the present invention exhibit higher oxygen transport with improved surface wettable properties when compared to silicone-polyether copolymers having linear alkyl linking groups. Moreover, the oxygen permeability of the hydrogel films or lenses can be tuned from 40 Dk to 400 Dk units by selecting the silicone monomers, independently or in combinations, of the present invention. The monomers and prepolymers employed in accordance with this invention are readily polymerized to form three-dimensional networks, which permit the transport of oxygen with improved wettability along with better mechanicals and optical clarity.

For example, the silicone hydrogel film produced with 50 wt. % of a monomer of the current invention (Example 1), 25 wt. % of DMA, 20 wt. % of HEMA and 5 wt. % of NVP co-monomer shows lower captive bubble contact angle (less than or equal to 40°) and low modulus <2 MPa compared to the silicone hydrogel film produced with corresponding silicone-polyether having linear alkyl linking groups, which shows, captive contact angle of 58° and modulus >2 MPa for compositions with HEMA. Similar trends were observed for silicone-hydrogels produced with different compositions of organic co-monomers and the inventive monomers.

Specific use of the films include intraocular contact lenses, artificial corneas, and soft disposable long-wear contact lenses or as coatings for biomedical devices.

In one aspect the hydrophilic silicone macromer can be used in preparation of homo or copolymers with other free radical polymerization effective monomers to form materials in bulk or latex form. These homopolymer, copolymer, emulsion and latex particles comprising the macromer of current invention can be used as ingredients in personal care formulations including skin care, hair care, and nail care, such as lipsticks, mascaras, foundations, lotions, creams, shampoos, conditioners and nail polishes, to improve their ware, tactile properties and ease of application. They also can be used in textile and fiber treatment applications to impart smooth, soft feel and wettability to both natural and synthetic fibers. Finally the homopolymer, copolymer, emulsion and latex particles can be incorporated into coating formulations for metal, plastic, wood and paper, such as varnishes, latex paints and roofing compositions.

Aspects of the invention may be further understood with reference to the following non-limiting examples.

EXAMPLES

Hydrophilic Silicone Monomers

Example 1

25 g of poly-allyl glycidyl ether-co-ethylene oxide copolymer containing 1.4 meq/g of hydroxyl and 1.49 meq/g of allyl content was taken in a reactor fitted with a condenser, dropping funnel and thermometer. The material was heated to 75° C. and reacted with 6.22 g of heptamethyltrisiloxane (MD'M) in the presence of 15 ppm of chloro-platinic acid and 50 ppm of dibutylethanol amine. The reaction was slightly exothermic and continued at 85° C. for 4 hours until all the hydride was consumed. After completion of hydrosilylation, 16.4 g of the silicone polyether produced above was mixed with 20 g of toluene and 2.8 g of triethyl amine in another reactor. The mix was then cooled to 5° C. in an ice bath and 2.64 g of methacryloyl chloride was added slowly to the mix. Upon addition, the reaction mixture turns opaque and was kept under stirring for 6-7 hours followed by filtration to remove the salt. The resulting solution is then subjected to stripping under reduced temperature to produce a methacrylate capped silicone polyether having a viscous clear appearance at ambient temperature.

Example 2

20 g of poly-allyl glycidyl ether-co-ethylene oxide copolymer containing 1.4 meq/g of hydroxyl and 1.49 meq/g of allyl content was taken in a reactor fitted with a condenser, dropping funnel and thermometer. The material was heated to 75° C. and reacted with 23.54 g of linear mono-functional hydride terminated polydimethylsiloxane with 0.93 meq/g of silanic hydrogen content (procured from Gelest Inc.) in the presence of 15 ppm of chloro-platinic acid and 50 ppm of dibutylethanol amine. The reaction was slightly exothermic and continued at 85° C. for 4 hours until all the hydride was consumed. After completion of hydrosilylation, 25 g of the silicone polyether produced above was mixed with 20 g of toluene and 2.5 g of triethyl amine in another reactor. The mix was then cooled to 5° C. in an ice bath and 2.3 g of methacryloyl chloride was added slowly to the mix. Upon addition of the methacryloyl chloride, the reaction mixture turns opaque and was kept under stirring for 6-7 hours followed by filtration to remove the salt. The resulting solution is then subjected to stripping under reduced temperature to produce a methacrylate capped silicone polyether having a viscous clear appearance at ambient temperature.

Example 3

A poly allylgycidylether-co-polyethyleneoxide-co-poly-allylglycidylether triblock copolymer was synthesized by reacting 30 g of PEG 600 with 17.2 g of allylglycidylether (AGE) in presence of NaOCH$_3$ as catalyst. The AGE was added to the catalyst and PEG600 mixture at 80° C. under N$_2$ blanket and mixed for 5 hours until no free AGE was available and then neutralized with acetic acid until the pH was 6.5-7.10 g of this block copolymer was then reacted with 4.5 g of MD'M with 10 ppm of Pt-catalyst and 50 ppm sodium propionate buffer at 80° C. until all the hydrides were consumed as confirmed by $^1$H-NMR. 10 g of the above mentioned silicone polyether was mixed with 20 g of toluene and 3.5 g of triethyl amine in another reactor. The mix was then cooled to 5° C. in an ice bath and 2.4 g of methacryloyl chloride was added slowly. Upon addition of methacryloyl chloride, the reaction mixture turns opaque and was kept under stirring for 6-7 hours followed by filtration to remove the salt. The resulting solution is then subjected to stripping under reduced temperature to produce a methacrylate capped silicone polyether having a viscous clear appearance at ambient temperature.

Example 4

75 g poly-allyl glycidyl ether-co-ethylene oxide copolymer containing 0.89 meq/g of hydroxyl and 2.1 meq/g of allyl content was taken in a reactor fitted with a condenser, dropping funnel and thermometer. The material was heated to 75° C. and reacted with 34.4 g of MD'M in the presence of 15 ppm of chloro-platinic acid and 50 ppm of dibutylethanol amine. The reaction was slightly exothermic and continued at 85° C. for 4 hours until all the hydride was consumed. After completion of hydrosilylation, 75 g of the above mentioned silicone polyether was mixed with 200 mL of toluene and 7.5 g of triethyl amine in another reactor. The mix was then cooled to 5° C. in an ice bath and 5.1 g of methacryloyl chloride was added slowly to the mix. Upon addition of methacryloyl chloride, the reaction mixture turns opaque and was kept under stirring for 6-7 hours followed by filtration to remove the salt. The resulting solution is then subjected to stripping under reduced temperature to produce a methacrylate capped silicone polyether having a viscous clear appearance at ambient temperature.

Example 5

50 g poly-allyl glycidyl ether-co-ethylene oxide copolymer containing 0.64 meq/g of hydroxyl and 2.68 meq/g of allyl content was taken in a reactor fitted with a condenser and thermometer. The material was heated to 75° C. and reacted with 12.4 g of heptamethyltrisiloxane (MD'M) in the presence of 30 ppm of Karstedt's catalyst and 70 ppm of sodium propionate. The reaction was slightly exothermic and continued at 105° C. until all the hydride was consumed. After completion of hydrosilylation, 55 g of the above mentioned silicone polyether was mixed with 126 g of toluene and 4.47 g of triethylamine in another reactor. The mix was then cooled to 5° C. in an ice bath and 3.89 g of methacryloyl chloride was added slowly to the mix. Upon addition, the reaction mixture turns opaque and was kept under stirring for 6-7 hours followed by filtration to remove the salt. The resulting solution is then subjected to stripping under reduced temperature to produce a methacrylate capped silicone polyether having a viscous clear appearance at ambient temperature.

Example 6

50 g poly-vinyl cyclohexyl epoxide-co-ethylene oxide copolymer containing 0.644 meq/g of hydroxyl and 3.41 meq/g of vinyl content was taken in a reactor fitted with a condenser and thermometer. The material was heated to 75° C. and reacted with 38 g of heptamethyltrisiloxane (MD'M) in the presence of 30 ppm of Karstedt's catalyst and 70 ppm of sodium propionate. The reaction was slightly exothermic and continued at 105° C. until all the hydride was consumed. After completion of hydrosilylation, 55 g of the above mentioned silicone polyether was mixed with 127 g of toluene and 4.51 g of triethyl amine in another reactor. The mix was then cooled to 5° C. in an ice bath and 3.92 g of methacryloyl chloride was added slowly to the mix. Upon addition, the reaction mixture turns opaque and was kept under stirring for 6-7 hours followed by filtration to remove the salt. The resulting solution is then subjected to stripping under reduced temperature to produce a methacrylate capped silicone polyether having a viscous clear appearance at ambient temperature.

Example 7

50 g pol-vinyl cyclohexyl epoxide-co-ethylene oxide copolymer containing 0.75 meq/g of hydroxyl and 2.6 meq/g of vinyl content was taken in a reactor fitted with a condenser and thermometer. The material was heated to 75° C. and reacted with 38 g of heptamethyltrisiloxane (MD'M) in the presence of 30 ppm of Karstedt's catalyst and 70 ppm of sodium propionate. The reaction was slightly exothermic and continued at 105° C. until all the hydride was consumed. After completion of hydrosilylation, 70 g of the above mentioned silicone polyether was mixed with 164 g of toluene and 6.51 g of triethyl amine in another reactor. The mix was then cooled to 5° C. in an ice bath and 5.66 g of methacryloyl chloride was added slowly to the mix. Upon addition, the reaction mixture turns opaque and was kept under stirring for 6-7 hours followed by filtration to remove the salt. The resulting solution is then subjected to stripping under reduced temperature to produce a methacrylate capped silicone polyether having a viscous clear appearance at ambient temperature.

Example 8

The synthesis involves four steps. Step 1: 50 grams of poly-allyl glycidyl ether-co-ethylene oxide copolymer containing 0.64 meq/g of hydroxyl and 2.68 meq/g of allyl content was taken in a reactor fitted with a condenser and thermometer. The material was heated to 75° C. and reacted with 12.4 grams of heptamethyltrisiloxane (MD'M) in the presence of 30 ppm of Karstedt's catalyst and 70 ppm of sodium propionate. The reaction was slightly exothermic and continued at 105° C. until all the hydride was consumed.

Step 2: 50 grams of the silicone polyether produced in Step 1 (50 grams, 0.023 moles) and triethylamine (9.4 mL, 0.068 moles) in a 500 mL three-neck round bottom flask fitted with a reflux condenser and a dropping funnel. The nitrogen gas is continuously purged during the reaction at rate of about 20 to 30 bubbles per second in a bubbler connected to the third neck of the flask using an adapter and a rubber tube. To a stirring reactant is added anhydrous tetrahydrofuran (60 mL) and stirring is continued. The reaction temperature is increased to 35° C. and maintained throughout the reaction. p-toluenesulfonyl chloride (5.6 g, 0.029 moles) solution in anhydrous tetrahydrofuran (25 mL) is added drop wise for 40 to 45 minutes. A white precipitate of triethylammonium hydrochloride salt precipitates out within 45 minutes of the reaction. The reaction time is 4 to 5 hours. After the reaction, organic salt is filtered out and the filtrate is concentrated under reduced pressure on a rotary evaporator. After removal of the solvent some more organic salt separates out of the product after storage for 12 hours at 27° C. Filtration resulted in a tosylate terminated silicone polyether in quantitative yield. This product is confirmed by the NMR technique.

Step 3: 25 grams (0.33 mol) of glycine is added pinch by pinch to 250 mL round bottom flask containing aqueous NaOH solution (34 grams, 0.83 moles) in 100 mL deionized water. The flask is cooled to 0 to 5° C. using ice-salt bath. Methacryloyl chloride (39 mL, 0.39 moles) is added drop wise for 30 to 45 minutes maintaining the bath temperature below 5° C. Then the reaction mixture is allowed to warm to room temperature. The reaction mixture is acidified to pH 3 and extracted 4 times with ethyl acetate (40 mL×4). The ethyl acetate layer is separated using a separating funnel and transferred to a conical flask containing anhydrous sodium sulfate (50 grams). The ethyl acetate is decanted to round bottom flask and the solvent is removed under reduced pressure to obtain glycine methacrylamide as a white solid powder (>70% yield). This product is confirmed by the NMR technique.

Step 4: The final step is a SN² (Substitution Nucleophillic 2) reaction step, and the tosylate terminated silicone polyether (25 grams, 0.011 moles) is reacted with 1,8-Diazabicyclo[5.4.0]undec-7-ene (DBU) (1.73 grams, 0.013 moles) and glycine methacrylamide (1.65 grams, 0.012 moles) using N,N-dimethylformamide (30 mL) as the solvent in a 250 mL two-neck round bottom flask fitted with a reflux condenser, heating bath and a nitrogen bubbler. One hundred to two hundred ppm of hydroquinone is used during the reaction to avoid unexpected polymerization. The temperature of the heating bath is maintained at 55° C. during the reaction. After 12 hours, N,N-dimethylformamide is removed under reduced pressure using a rotary evaporator (60° C., 20 mbar). The crude material is dissolved in 25 mL chloroform and washed with brine solution (15 mL×3). The chloroform layer is separated, dried over anhydrous Na₂SO₄, decolorized from activated charcoal, and the solvent is removed under reduced pressure in a rotary evaporator. The final product is obtained in quantitative yield.

The final product is well characterized by infrared spectroscopy, multinuclear NMR ($^1$H, $^{13}$C, $^{29}$Si) spectroscopy Silicone Hydrogel Formulation (H1-H10)

Silicone hydrogel formulations were prepared by thermal and UV curing from mixing the macromer according to present invention with HEMA (2-hydroxyethyl methacrylate), DMA (N,N-Dimethylacrylamide) and NVP (N-vinylpyrrolidone) and EGDMA (ethylene glycol dimethacrylate) cross-linker in various amounts. The initiators used are 0.5% by weight of BPO (benzoyl Peroxide) (at temperature of 85° C. for 4 hours) and 0.5% by weight of 2-hydroxy-2-methyl propiophenone (HMPP) or Irgacure 819 (UV curing was done in a Dymax flood system for about 90 s). Table 1 shows the hydrogel formulations H1-H10 and the properties of those polymers listed.

be limited to the particular embodiments disclosed as the best mode for carrying out this invention, but that the invention will include all embodiments falling within the scope of the appended claims. All citations referred herein are expressly incorporated herein by reference.

What is claimed is:

1. A composition comprising at least one hydrophilic silicone macromer of the Formula:

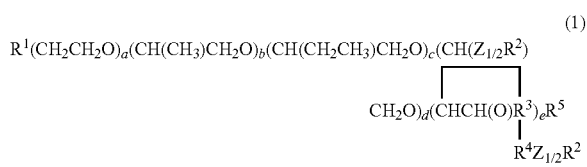

where $R^2$ is a group defined as $M_fD_gT_hQ_iR^6_j$ with $M=R^7R^8R^9SiZ_{1/2}$, $D=R^{10}D^{11}SiZ_{2/2}$, $T=R^{12}SiZ_{3/2}$, $Q=SiZ_{4/2}$, $R^6=-(CH_2)_{1/2}(R^{13})_k(CH_2)_{1/2}-$; $R^1$ is independently selected from $-OH$, $-OC(O)R^{15}$, Y, or $-OR^{15}$; $R^5$ is independently selected from hydrogen, a $-C(O)R^{15}$ group, Y, or a monovalent hydrocarbon radical having from about 1 to about 40 carbon atoms that optionally contain a heteroatom and/or a hydroxyl group; at least one of $R^1$ and $R^5$ is Y; Y is a free radical polymerizable group; Z is O or $CH_2$ group subject to the limitation that the macromer contains an even number of $O_{1/2}$ and an even number of $(CH_2)_{1/2}$ groups and they both are all paired in the molecule; $R^3$ is a trivalent hydrocarbon radical having 1 to about 40 carbon atoms that optionally contain a heteroatom and/or a hydroxyl group; $R^7$, $R^8$, $R^9$, $R^{10}$, $R^{11}R^{12}$ and $R^{15}$ are each independently selected from $OR^{14}$, a monovalent hydrocar-

TABLE 1

| Reactants | H1 | H2 | H3 | H4 | H5 | H6 | H7 | H8 | H9 | H10 |
|---|---|---|---|---|---|---|---|---|---|---|
| Example 1 | 49.8 | | | | | | | | | |
| Example 2 | | 49.8 | | | | | | | | |
| Example 3 | | | 24.9 | | | | | | | |
| Example 4 | | | | 49.8 | | 24.9 | 49.8 | | | |
| Example 5 | | | | | 69.5 | | | | | |
| Example 6 | | | | | | | | 49.5 | | |
| Example 7 | | | | | | | | | 24.8 | |
| Example 8 | | | | | | | | | | 79.6 |
| TRIS | | | | | | | | 24.8 | | |
| HEMA | 19.9 | 19.9 | 19.9 | 19.9 | | | 19.9 | | 24.8 | |
| DMA | 24.9 | 24.9 | 24.9 | 24.9 | 29.8 | 29.9 | 24.9 | 39.6 | 19.8 | 19.9 |
| NVP | 5 | 5 | 5 | 5 | | 19.9 | 5 | 9.9 | 5 | |
| Y-16* | | | 24.9 | | | 24.9 | | | | |
| EGDMA | | | | | 0.2 | | | | 0.5 | 0.5 |
| BPO | 0.5 | 0.5 | | | | 0.5 | | | | |
| HMPP | | | 0.5 | 0.5 | 0.5 | | | 0.5 | 0.5 | 0.5 |
| Cured Film Properties | | | | | | | | | | |
| Appearance | Clear | Clear | Clear | Clear | Clear | Clear | Clear | Clear | Clear | Clear |
| Contact angle (deg) | 42 ± 2 | 42 ± 2 | 23 ± 2 | NM | 28 ± 2 | 20 ± 2 | NM | 20 ± 2 | 33 ± 2 | 15 ± 2 |
| Water Content (wt. %) | 64 ± 2 | 45 ± 2 | 53 ± 2 | 58 ± 2 | 57 ± 1 | 70 ± 2 | 57 ± 2 | 60 ± 1 | 40 ± 1 | 56 ± 1 |
| Modulus/MPa | 2 ± 0.5 | 5 ± 1 | 2.6 ± 0.2 | 2 ± 0.5 | 1 ± 0.2 | 1.9 ± 0.5 | 2.0 ± 0.5 | 1.5 ± 0.2 | 1.6 ± 0.2 | 1.1 ± 0.2 |

*Y-16 is a monofunctional silicone acrylate molecule obtained from Momentive Performance Materials, Inc.
NM is not measured.

While the invention has been described with reference to various embodiments, those skilled in the art will understand that various changes may be made and equivalents may be substituted for elements thereof without departing from the scope of the invention. It is intended that the invention not bon radical having 1 to about 20 carbon atoms that optionally contain a heteroatom and/or a hydroxyl group; $R^4$ is a divalent, linear, or branched unsaturated or saturated hydrocarbon radical containing at least one and less than about 30 carbon atoms that optionally contain a heteroatom and/or a hydroxyl group; $R^{13}$ is oxygen or divalent linear or branched unsaturated or saturated hydrocarbon radicals containing at least one and less than about 30 carbon atoms that optionally contain a heteroatoms and/or a hydroxyl group; $R^{14}$ is a monovalent, linear or branched unsaturated or saturated hydrocarbon radical having 1 to about 20 carbon atoms that optionally contain a heteroatom and/or hydroxyl group; a+e>2; b, c, and d are zero or positive subject to the limitation 3<a+b+c+d+e<about 1000; d+e>1; f, g, h, i and j are 0 or positive subject to the limitation f+g+h+i+j<about 300; f+g+h+i is greater than 0; and k is 0 or 1.

2. The composition of claim 1, wherein the hydrophilic silicone macromer has a structure according to the formula $R^1(CH_2CH_2O)_a(CH(CH_3)CH_2O)_b(CH[CH_2]_{1/2}R^2]CH_2O)_d R^5$.

3. The composition of claim 2, where $R^2$ is a group defined as $M_fD_gT_hQ_iR^6_j$ with $M=R^7R^8R^9Si(O)_{1/2}$; $D=R^{10}Si(O)_{2/2}(CH_2)_{1/2}$; f=2; g=1; h=0; i=0; j=1; and $R^6=\!\!-\!\!(CH_2)_{1/2}R^{13}(CH_2)_{1/2}$.

4. The composition of claim 2, where $R^2$ is a group defined as $M_fD_gT_hQ_iR^6_j$ with $M=R^7R^8R^9Si(O)_{1/2}$; $T=Si(O)_{3/2}(CH_2)_{1/2}$; f=3; g=0; h=1; i=0; j=1; and $R^6=\!\!-\!\!(CH_2)_{1/2}R^{13}(CH_2)_{1/2}\!\!-\!\!$.

5. The composition of claim 2, where $R^2$ is a group defined as $R^7R^8R^9SiO(Si(R^{10})(R^{11})(O)_iSi(R^7)(R^8)(CH_2)_{1/2}$; and where 0≤l≤200.

6. The composition of claim 1, wherein the hydrophilic macromer has a structure according to the formula:

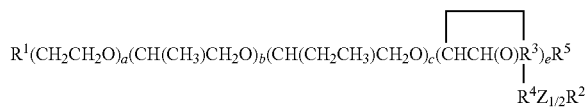

wherein $R^2$ is a group defined as $R^7R^8R^9SiO(Si(R^{10})(R^{11})O)_iSi(R^7)(R^8)(CH_2)_{1/2}$; and where 0≤l≤200.

7. The composition of claim 1, wherein the hydrophilic macromer is of the formula:

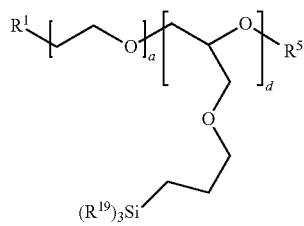

(7)

wherein $R^1$ is independently selected from —OH, —OC(O)$R^{15}$, —OR$^{15}$, or Y; $R^5$ is independently selected from hydrogen, a —C(O)R$^{15}$ group, a monovalent hydrocarbon radical having from about 1 to about 40 carbon atoms that optionally contains a heteroatom and hydroxyl group, or Y; Y is a free radical polymerizable group subject to the limitation that at least one of $R^1$ and $R^5$ is Y; $R^{19}$ is independently selected from linear, branched, or cyclic mono-valent radicals with 1 to 100 carbon atoms that may contain a heteroatom chosen from halogens, oxygen, nitrogen, or siloxane radicals containing 1 to 50 Si—O linear or cyclic linkages; a and d are non-zero integers such that 2≤a+d≥1000.

8. The composition of claim 1, wherein the hydrophilic macromer is of the formula:

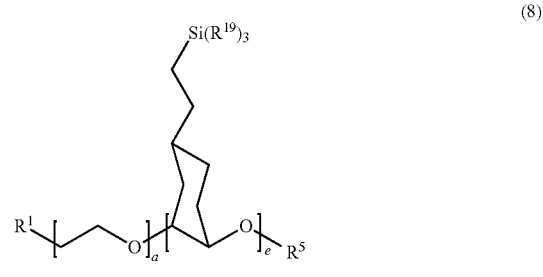

(8)

wherein $R^1$ is independently selected from —OH, —OC(O)$R^{15}$, —OR$^{15}$, or Y; $R^5$ is independently selected from hydrogen or a —C(O)R$^{15}$ group or a monovalent hydrocarbon radical having from about 1 to about 40 carbon atoms that optionally contains a heteroatom and a hydroxyl group, or Y; Y is a free radical polymerizable group subject to the limitation that at least one of $R^1$ and $R^5$ is Y; $R^{19}$ is independently selected from linear, branched, or cyclic mono-valent radicals with 1 to 100 carbon atoms that optionally contain heteroatoms chosen from halogens, oxygen, nitrogen, or siloxane radicals containing 1 to 50 Si—O linear or cyclic linkages; a and d are non-zero integers such that 2≤a+e≥1000.

9. The composition of claim 1, wherein Y is chosen from a polymerizable group having the general structure:

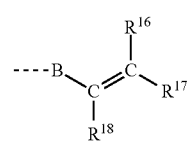

wherein $R^{16}$, $R^{17}$ and $R^{18}$ can be selected from hydrogen, a monovalent alkyl group with 1 to 10 carbon atoms and may optionally contain heteroatoms; —COOH; and —CH$_2$COOH; and the linking group B is chosen from a divalent radical containing 1 to 20 carbon atoms that can optionally contain heteroatoms.

10. The composition of claim 9, where the linking group B is chosen from the following functional moieties:

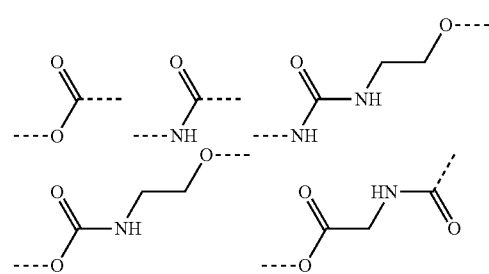

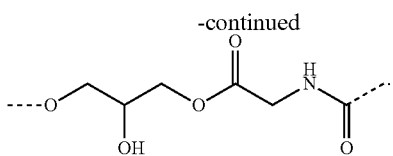

11. The composition of claim 1, wherein the composition is a hydrogel forming composition.

12. The composition of claim 11, wherein the hydrogel forming composition further comprises a monomer chosen from a vinylic monomer, an acrylide monomer, an acrylic monomer, or a combination of two or more thereof; a free radical initiator; and optionally a cross-linker.

13. The composition of claim 12, wherein the vinylic monomer is chosen from N-vinyl-pyrrolidone (NVP), N-vinyl-caprolactam, N-vinyl-acetamide, N-vinyl-formamide and N-vinyl-isopropylamide, vinyl benzene, vinyl naphthalene, vinyl pyridine, vinyl alcohol, a vinyl containing silicone, or a combination of two or more thereof.

14. The composition of claim 12, wherein the acrylic monomers are chosen from 2-hydroxy-ethyl-methacrylate (HEMA), 2-hydroxy-ethyl-acrylate (HEA), hydroxyl propyl methacrylate, trimethylammonium 2-hydroxy propyl methacrylate hydrochloride, dimethylaminoethyl methacrylate, glycerol methacrylate, N,N-dimethylacrylamide (DMA), N-isopropylacrylamide, acrylamide, methacrylamide, acrylic acid, methacrylic acid, or a combination of two or more thereof.

15. The composition of claim 12, wherein the initiator can be a thermal or a photo initiator chosen from 2,2'-azobis (2,4-dimethylpentanenitrile), 2,2'-azobis (2-methylpropanenitrile), 2,2'-azobis (2-methylbutanenitrile), peroxides benzoin methyl ether, diethoxyacetophenone, a benzoylphosphine oxide, 2-hydroxy-2-methyl propiophenone (HMPP), 1-hydroxycyclohexyl phenyl ketone, an acylphosphine oxide, or a combination of two or more thereof.

16. The composition of claim 12, wherein the cross-linker can be selected from ethylene glycol dimethacrylate and trimethyloylpropane trimethacrylate, diethyleneglycol dimethacrylate, bisphenol A dimethacrylate, diglycidyl bisphenol A dimethacrylate and dimethacrylate-terminated polyethylene glycol and reactive linear polyether modified silicones, or a combination of two or more thereof.

17. A contact lens comprising the composition of claim 11.

18. The contact lens according to claim 17 comprising a limited extraction protocol that further comprises a green or aqueous solvents chosen from water, an organic or inorganic salt solution, a buffer, an emulsion, a commercial lens cleaning solution, or any ophthalmically compatible solvent in the temperature range of 15-125° C. for extraction.

19. A polymer formed from the composition according to claim 1.

20. The polymer of claim 19, wherein the polymer is a homopolymer, copolymer, free-radical polymerized emulsion, or a latex composition.

21. A composition comprising the polymer of claim 19 wherein the composition is a film forming additive in a textile, paper, leather, personal care, health care, home care, coating, painting or seed treatment formulation.

* * * * *